United States Patent [19]

Zeldin

[11] Patent Number: 4,855,433
[45] Date of Patent: Aug. 8, 1989

[54] SILANES

[75] Inventor: Martel Zeldin, Indianapolis, Ind.

[73] Assignee: Indiana University Foundation, Bloomington, Ind.

[21] Appl. No.: 174,249

[22] Filed: Mar. 29, 1988

[51] Int. Cl.[4] .......................... B01J 31/02; C07F 7/10
[52] U.S. Cl. ...................................... 546/14; 502/232
[58] Field of Search ........................................... 546/14

[56] References Cited

U.S. PATENT DOCUMENTS

| | | | |
|---|---|---|---|
| 2,854,455 | 9/1958 | Cislak | 546/14 |
| 2,924,601 | 2/1960 | Brown | 546/14 |
| 3,466,270 | 9/1969 | Cook | 546/14 |
| 4,024,129 | 5/1977 | Henniger et al. | 546/14 |

FOREIGN PATENT DOCUMENTS 685186  12/1952  United Kingdom .................. 546/14

OTHER PUBLICATIONS

Fife, W. K., et al., J. Am. Chem. Soc., 1987, 109, 1278–79, (1983).
Scriven, E. F., Chem. Soc. Rev., 12:129–161, (1983).
Fife, W. K. and Dally, R. D., Amer. Chem. Soc. Abst. 187:251, (1984).
Mathias, L. J. and Vaidya, R. A., J. Am. Chem. Soc., 108:1093–1094, (1986).
Hofle et al., Agnew Chem. Int. Ed. Engl., 17:569–583, (1978).
Shai et al., J. Am. Chem. Soc., 107:4249–4252, (1985).
Cook et al., J. Am. Chem. Soc., 88, 3396–3403, (1966).
Sulzbach, J. Organometal. Chem., 24, 307–314, (1970).
Wittenberg et al., Chem. Ind. (London), 390–391, (1958).
Anderson et al., Chem. Ind. (London), 505, (1964).
Zeldin et al., "Pyridinyl Containing Silane Monomers and Siloxane Dimers and Polymers", No Journal cited, No Date cited.

*Primary Examiner*—Robert T. Bond
*Attorney, Agent, or Firm*—Kirkland & Ellis

[57] ABSTRACT

Novel silylpyridine monomers and dimers and their N-oxide derivatives and poly(methylpyridinylsiloxane) polymers and copolymers and their N-oxide derivatives have utility as inverse phase transfer catalysts.

9 Claims, No Drawings

SILANES

BACKGROUND OF THE INVENTION

A. Field of the Invention

This invention relates to the synthesis of inverse phase transfer catalysts. These catalysts comprise water insoluble silane monomers, disiloxanes, oligomeric-, polymeric- and copolymeric siloxanes containing pyridine or pyridine 1-oxide pendant groups.

B. Prior Art

Water soluble monomers and polymers containing pyridine and pyridine 1-oxide groups have been shown to serve as extremely active and selective nucleophilic catalysts in a variety of organic reactions: e.g., transacylation of derivatives of carbon, sulfur and phosphorus acids. A unique aspect of these catalysts is their ability to facilitate the synthesis in high yield of extremely water sensitive materials (e.g., mixed and symmetrical organic acid anhydrides) in mixed aqueous/organic solvents by product phase-transfer.

It is an object of the present invention to provide a method of synthesis of water insoluble, organic solvent soluble inverse phase-transfer catalysts containing pyridine or pyridine 1-oxide units on silicon monomers, disiloxanes, oligomeric-, polymeric- and copolymeric siloxanes.

It is a further object of the invention to create inverse phase-transfer catalysts which faciliate the synthesis in high yields of extremely water sensitive materials in aqueous/organic solvent suspensions or emulsions by product phase-transfer.

SUMMARY OF THE INVENTION

The foregoing objects, advantages and features of the present invention may be achieved with the preparation of inverse phase-transfer catalysts. Thus, pyridine and pyridine 1-oxide containing silanes, disiloxanes, oligomeric-, polymeric- and copolymeric siloxanes have been prepared.

DETAILED DESCRIPTION OF THE INVENTION

A. Synthesis of Pyridine and Pyridine 1-Oxide Containing Silanes and Disiloxanes Pyridine and pyridine 1-oxide containing monomers of the structural formula:

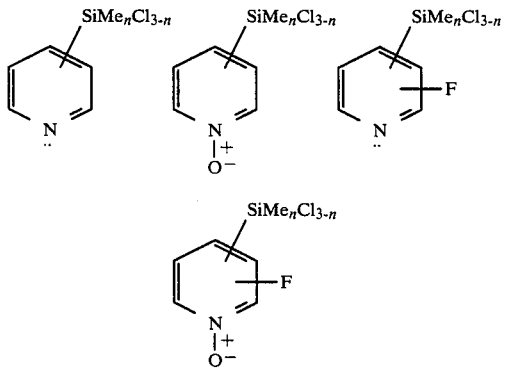

are prepared by reacting a halogenated (preferably Br) pyridine with a lithiating reagent (e.g., n-Bu Li, PhLi, $R_2NLi$ (R=Me, Et, Pr, i-Pr)) at low temperatures, preferably near $-76°$ C., in an organic solvent, preferably diethylether or tetrahydrofuran (THF). This lithiated mixture is then added slowly to an excess (preferably a ten-fold excess) of a silane of the formula, $Me_n\text{-}SiCl_{4-n}$ (where n=1,2,3). The organic solvent and excess unreacted chlorosilane are removed by vacuum evaporation giving a liquid which is then purified by vacuum distillation. The pure product is a colorless liquid which is soluble in organic solvents (aliphatic or aromatic), and reacts with protonic solvents (such as alcohols, primary and secondary amines and water). The product is obtained in 50–80% yield and can be characterized by conventional spectroscopic methods.

In addition, disiloxanes may be prepared by hydrolyzing the above mono-functional pyridinylsilanes with aqueous ammonia solution, the ammonia solution being added slowly with vigorous stirring. The resulting dispersion is treated with saturated aqueous $KHCO_3$ solution and the disiloxane is obtained as a separated layer or, may be extracted from the water phase with an organic solvent such as toluene. The solution is dried over anhydrous $KHCO_3$ and the toluene is removed under vacuum. The residual fluid is purified by vacuum distillation. The products are colorless liquids or low-melting solids at ambient temperatures. They have been characterized by conventional spectroscopic methods.

EXAMPLE I

1. Synthesis of 2-Fluoro-3-chlorodimethylsilylpyridine

Dry diisopropylamine (0.189 mol) in dry THF (75 ml) was stirred under argon at $-76°$ C. in a 250 ml 3-neck round-bottom flask fitted with a dropping funnel, mechanical stirrer and a low temperature thermometer. n-Butyl lithium (75 ml; 2.51M in hexane) mixed with THF (15 ml) was added dropwise to the above mixture. The resulting mixture was stirred for 20 minutes at $-76°$ C. and 2-fluoropyridine (0.189 mol), dissolved in THF (45 ml) was added slowly. The yellow suspension was stirred for 30 min. at $-76°$ C. and poured under argon into a jacketed dropping funnel which was cooled with dry ice/acetone. The suspension was then added dropwise to excess $Me_2SiCl_2$ (4.72 mol) at $-76°$ C. under argon. The mixture was stirred for 30 min. and allowed to warm to room temperature. Volatile solvents and unreacted $Me_2SiCl_2$ were removed under vacuum at room temperature. The residual material was distilled twice to give a colorless liquid: (19.3 g; yield 54%; b.p. 33°–35° at 0.5 torr).

2. Synthesis of 1,1,3,3-Tetramethyl-1,3-bis(2-fluoropyridin-3-yl) Disiloxane (dimer)

In order to synthesize the dimer, a 250 ml round-bottom flask equipped with a dropping funnel and a mechanical stirrer was charged with 2-fluoro-3-chlorodimethylsilylpyridine (74 mmol) and toluene (20 ml). Aqueous ammonia (30 ml, 30%) was added dropwise with vigorous stirring. After addition, the toluene layer was separated and the aqueous layer was extracted with several 20 ml portions of toluene. The toluene fractions were combined, dried over anhydrous $KHCO_3$, filtered and the toluene was removed under vacuum. The resulting pale yellow fluid was distilled under vacuum to give a colorless liquid which solidified to colorless needles. The liquid was identified as the disiloxane: (Yield 56%; m.p. 41°–42° C. b.p. 142°–145° at 0.4 torr).

EXAMPLE II

1. Synthesis of 3-Fluoro-4-chlorodimethylsilylpyridine

The 3-fluoropyridine was reacted with the lithiating agent and $Me_2SiCl_2$ in the same manner as described in part 1 of Example I. The resulting colorless liquid was determined to be 3-fluoro-4-chlorodimethysilylpyridine: (Yield 55%: b.p. 63°–64° C. at 1 torr).

2. Synthesis of 1,1,3,3-Tetramethyl-1,3-bis(3-fluoropyridin-4-yl) Disiloxane The 3-fluoro-4-chlorodimethylsilylpyridine (22 mmol) was hydrolyzed in the manner described in part 2 of Example I above. The disiloxane product thus produced is a colorless liquid which solidified to needle crystals: (Yield 73%; m.p. 35°–37° C.; b.p. 107°–108° C. at 0.2 torr).

EXAMPLE III

1. Synthesis of 3-Dimethylchlorosilylpyridine

To a magnetically stirred solution of n-butyllithium (2.51M in hexane, 50 ml) in dry ether (80 ml) under argon at −76° C. in a 250 ml round-bottom flask was added 3-bromopyridine (0.126 mol) in ether (40 ml). The mixture was stirred for 1 hour. The resulting yellow suspension was added dropwise to a solution of $Me_2SiCl_2$ (0.983 mol) at −76° C. under argon through a jacketed dropping funnel cooled with dry ice/acetone. The mixture was contained in a 1 liter round-bottom flask. The mixture was stirred for an hour and warmed to ambient temperature. Volatiles were removed under vacuum. The residue was distilled to give the colorless liquid, 3-dimethylchlorosilylpyridine: (Yield 12.8 g or 59%; b.p. 42°–46° C. at 0.5 torr).

2. Synthesis of the 1,1,3,3-Tetramethyl-1,3-bis(pyridin-3-yl)disiloxane

The 3-dimethylchlorosilylpyridine (8.5 g) was placed in a 50 ml, round-bottom flask. Aqueous ammonia (30%) was added with vigorous stirring. Addition of the ammonia was continued until no further turbidity developed. The resulting mixture was extracted with toluene. The toluene phase was dried over anhydrous $K_2CO_3$, filtered and evaporated under vacuum to give a clear yellow liquid. The liquid was then distilled under vacuum giving a clear colorless liquid or the disilane which was characterized spectroscopically as the disiloxane: (Yield: 5.2 g or 72%; b.p. 125°–128° C. at 0.2 torr).

EXAMPLE IV

Synthesis of 1,1,3,3-Tetramethyl-1,3-bis(pyridin-2-yl)disiloxane

The procedure is identical to that described in subparts 1 and 2 of Example III above: (Yield 46%; b.p. 103°–105° C. at 0.1 torr).

B. Synthesis of N-oxides of the Silane Monomers and the Siloxane Dimers

N-oxides of the silane monomers and the siloxane dimers were prepared by stirring the pyridinyl containing compounds in the above examples with m-chloroperoxybenzoic acid (or other organic peroxide) in an organic solvent (preferably methylene chloride) at ambient temperature.

EXAMPLE V

1. Synthesis of 1,1,3,3-Tetramethyl-1,3-bis(1-oxypyridin-3-yl)disiloxane

In a typical experiment the dimer (0.58 g) from Example III, subpart 2 was dissolved in $CH_2Cl_2$ (5 ml) in a 50 ml round-bottom flask. M-Chloroperoxybenzoic acid (0.69 g) dissolved in $CH_2Cl_2$ (10 ml) was added. The mixture was stirred for several hours at ambient temperature. Aqueous saturated $K_2CO_3$ was added until no further precipitate formed. The white solids were removed by filtration and were washed with $CH_2Cl_2$ (5 ml). The solution was dried over anhydrous $K_2CO_3$ and the solvent was removed by vacuum evaporation to give a pale yellow liquid which was characterized by spectroscopic methods: (yield 0.54 g, 84%).

2. Synthesis of 1,1,3,3-Tetramethyl-1,3-bis(1-oxypyridin-2-yl)disiloxane

The procedure is identical to that described in subpart 1 of this Example above: (Yield 90%).

D. Synthesis of Oligomeric and Polymeric Siloxanes Containing Pyridine and 1-Oxypyridine Substituents Pyridine substituted oligomeric and polymeric siloxanes may be prepared by hydrolysis of pyridinyl substituted dihalomethylsilanes with aqueous ammonia.

EXAMPLE VI

Typically, a pyridine substituted dihalomethylsilane such as 3 dichloromethylsilylpyridine (0.97 g), which can by synthesized by the method previously described in Example III, subpart 1 above, using $MeSiCl_3$ as a silane reagent (yield: 50%), dissolved in a solvent such as toluene (6 ml). Aqueous ammonia (preferably 30%) is added with vigorous stirring until a permanent turbidity is developed. The toluene layer is separated and the water layer is extracted with fresh toluene. The toluene solution fractions are combined and dried. Subsequent evaporation of the solvent leaves a colorless fluid (0.85 g). The molecular weight (Mn) of the resulting polymer depends on the polymerization method and can range from 800–5000 (oligomers) to 20,000 (polymers). Higher molecular weights can be achieved by heating under vacuum to evolve water by bimolecular condensation. The oligomers and polymers are soluble in organic solvents and only very slightly soluble in water.

In addition, these polymers can be end-blocked with trimethylsiloxyl groups by refluxing with $(Me_3Si)_2NH$, $Me_3SiCl$ or other end-blocking reagents in an inert solvent such as toluene or xylene. The end-functional and end-blocked polymers are stable in nitrogen and argon to 450°–500° C. depending on molecular weight and purity.

EXAMPLE VII

The end-functional and end-blocked polymers can be N-oxidized with m-chloroperoxybenzoic acid or other organic peroxide in the manner described in Section B, part 1 above for the dimer. Typically 0.35 g of a low molecular oligomer (Mn 850), as previously described in Example V, was dissolved in $CH_2Cl_2$ (3 ml) in a 25 ml round-bottom flask. m-Chloroperoxybenzoic acid (0.44 g) dissolved in $CH_2Cl_2$ (7 ml) was added. The mixture was stirred for several hours at room temperature.

Aqueous saturated $K_2CO_3$ solution was added dropwise until neutral pH was reached. The mixture was filtered and the organic layer was separated and dried with anhydrous $K_2CO_3$ (potassium carbonate) the solids were filtered and $CH_2Cl_2$ layers was removed by evaporation to give a pale yellow fluid: (yield, 92%). Product was characterized as a N-oxide by spectroscopy. The N-oxide products are pale yellow fluids obtained in yields exceeding 90%. In a similar manner as described in section D above, 2- and 4-dichloromethylsilylpyridine can be synthesized and hydrolyzed with aqueous ammonia to give the corresponding oligomers and polymers. The oligomers and polymers can be oxidized to the 1-oxypyridinyl derivatives as described previously.

E. Synthesis of Poly(methyl 3-(1-oxypyridin-3-yl)siloxane-co-dimethylsiloxane)

Hydrolysis of dichloromethylpyridinylsilanes (2-, 3- or 4-substitution) with $RR^1SiCl_2$ (where R=alkyl, H, $R^1$=alkyl, aryl) with aqueous ammonia as described in section A above, gives a copolymer, where x and y depend on the relative quantity of the respective starting difunctional monomer.

The copolymer can also be prepared by hydrolysis of a mixture containing the hydroxy-terminated oligomer $(H+OSiMePy)_aOH)$ described in section D above with $RR'SiCl_2$ to give a structure:

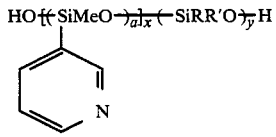

where a=5-15 and x/y depends on the ratio of the oligomer to $RR'SiCl_2$.

End-blocking of the aforementioned copolymer can be achieved by subsequent treatment with $(Me_3Si)_2NH$ or $Me_3SiCl$ or by inclusion of $(Me_3Si)_2O$ in the hydrolysis medium. The molecular weight of the copolymer depends on the post-heat-treatment or the quantity of $(Me_3Si)_2O$ used and ranged from $5\times10^3-2\times10^5$. The copolymers can be characterized by spectroscopy. Thermal stability depends on the quantity and the type of substituent (R, R') in the copolymer, the molecular weight and the nature of the end-groups. The copolymers can be N-oxidized in a manner similar to that described in Example VII above.

EXAMPLE VIII

1. Synthesis of Poly(methyl 3-(1-oxypyridin-3-yl)siloxane-co-dimethylsiloxane)

Typically, oligomer $H(OSiMe)_aOH$ (Mn=1114, a=8, 0.45 g), $(Me_2SiO)_4$ (0.24$_g$), $(Me_3Si)_2O$ (6.5 mg) and toluene (8 ml) are combined in a 25 ml round-bottom flask fitted with a reflux condenser. The mixture is stirred and refluxed under argon and 1 drop of a saturated aqueous KOH solution is added. The toluene-$H_2O$ azeotrope is removed by distillation. The reaction mixture is cooled to room temperature and washed with several ml of water. Toluene is removed under vacuum to give 0.60 g of a viscous colorless fluid (Mn=17,000). The fluid is dissolved in $CH_2Cl_2$ in a 25 ml round-bottom flask. m-Chloroperoxybenzoic acid (0.3 g) dissolved in $CH_2Cl_2$ (4 ml) is added and the mixture is stirred at room temperature for 8 hours. The solution is washed with saturated aqueous $K_2CO_3$ (5 ml) and filtered through a bed of anhydrous $K_2CO_3$. The organic layer is separated and the solvent is removed by rotoevaporation to give 0.58 g of a viscous pale-yellow fluid which was characterized as the N-oxide derivative by spectroscopic methods.

While the foregoing has been described with respect to preferred embodiments and alternatives thereto, they are not intended nor should they be construed as limitations on the invention. As one skilled in the art would understand, many variations and modifications of these embodiments may be made which fall within the spirit and scope of this invention.

What we claim is:

1. A silylpyridine monomer selected from the group consisting of chloromethylsilylpyridines of the formula:

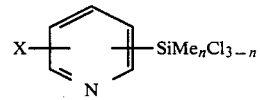

where n is 1 or 2; X is hydrogen or fluorine; and Me is methyl, and N-oxides thereof.

2. 2-Fluoro-3-chlorodimethylsilylpyridine, as claimed in claim 1.

3. 3-Fluoro-4-chlorodimethylsilylpyridine, as claimed in claim 1.

4. 3-Dimethylchlorosilylpyridine, as claimed in claim 1.

5. 3-Methyldichlorosilylpyridine, as claimed in claim 1.

6. 3-Methyldichlorosilylpyridine-N-oxide, as claimed in claim 1.

7. 3-Fluoro-4-chlorodimethylsilylpyridine-N-oxide, as claimed in claim 8.

8. 3-Dimethylchlorosilyllpyridine-N-oxide, as claimed in claim 1.

9. 3-Methyldichlorosilylpyridine-N-oxide, as claimed in claim 1.

* * * * *

UNITED STATES PATENT AND TRADEMARK OFFICE
CERTIFICATE OF CORRECTION

PATENT NO. : 4,855,433

DATED : August 8, 1989

INVENTOR(S) : Martel Zeldin

It is certified that error appears in the above-identified patent and that said Letters Patent is hereby corrected as shown below:

Column 5, line 5, "layers" should be -- layer --.

Column 6, line 50, "Claim 8" should be --Claim 1 --.

Signed and Sealed this

Thirty-first Day of July, 1990

Attest:

HARRY F. MANBECK, JR.

*Attesting Officer*  *Commissioner of Patents and Trademarks*

UNITED STATES PATENT AND TRADEMARK OFFICE
CERTIFICATE OF CORRECTION

PATENT NO. : 4,855,433

DATED : August 8, 1989

INVENTOR(S) : Dr. Martel Zeldin

It is certified that error appears in the above-identified patent and that said Letters Patent is hereby corrected as shown below:

Column 6, line 51    "Dimethylchlorosilyllpyridine-N-oxide" should be
--Dimethylchlorosilylpyridine-N-oxide--

Signed and Sealed this

Twenty-sixth Day of November, 1991

Attest:

HARRY F. MANBECK, JR.

*Attesting Officer*    *Commissioner of Patents and Trademarks*